United States Patent [19]

Yoshida

[11] Patent Number: 4,775,889
[45] Date of Patent: Oct. 4, 1988

[54] BOTTLE MOUTH DEFECT INSPECTION APPARATUS

[75] Inventor: Hajime Yoshida, Tokyo, Japan

[73] Assignee: Hajime Industries Ltd., Tokyo, Japan

[21] Appl. No.: 907,038

[22] Filed: Sep. 12, 1986

[30] Foreign Application Priority Data

Sep. 21, 1985 [JP] Japan .................. 60-209600

[51] Int. Cl.$^4$ .............................................. H04N 7/18
[52] U.S. Cl. .................................... 358/106; 358/101;
250/223 B; 356/240; 356/428
[58] Field of Search ................ 358/101, 106, 107;
209/526; 250/223 B; 356/240, 428; 362/308,
311

[56] References Cited

U.S. PATENT DOCUMENTS

| 3,386,579 | 6/1968 | Schulze et al. | 250/224 |
| 4,026,414 | 5/1977 | Ellingu | 356/240 |
| 4,208,130 | 6/1980 | Saconney et al. | 356/428 |
| 4,391,373 | 7/1983 | Wiggins | 250/223 B |
| 4,454,542 | 6/1984 | Miyazawa | 358/106 |
| 4,606,635 | 8/1986 | Miyazawa et al. | 356/240 |

FOREIGN PATENT DOCUMENTS 2916361 11/1980 Fed. Rep. of Germany ...... 358/101

Primary Examiner—James J. Groody
Assistant Examiner—John K. Peng
Attorney, Agent, or Firm—Bauer & Schaffer

[57] ABSTRACT

A bottle mouth defect inspection apparatus having a ring-shaped light source for irradiating a ring-shaped bottle mouth portion to be inspected, a photo-electric conversion sensor for converting a reflected light from the bottle mouth portion into an electrical signal and an electronic processor for processing the electrical signal to thereby inspect the existence or not of defects on the bottle mouth portion, wherein the diameter of the ring-shaped light source is selected larger than the outer diameter of the bottle mouth portion, the optical axis of the photo-electric conversion sensor, the center axis of the ring-shaped light source and the center axis of the bottle mouth portion are coincided to each other, positions of the photo-electric conversion sensor, the ring-shaped light source and the bottle mouth portion along the axis are selected such that only the ring-shaped reflected lights from the outer and inner edge portions of the bottle mouth portion are incident on the photo-electric conversion sensor as a dual ring-shaped light and then converted to an electrical signal and then, this electrical signal is processed by the electronic processor to thereby carry out the above inspection.

6 Claims, 2 Drawing Sheets

BOTTLE MOUTH DEFECT INSPECTION APPARATUS

BACKGROUND OF THE INVENTION

1. Field of the Invention

The present invention relates generally to a bottle mouth defect inspection apparatus and more specifically to a bottle mouth defect inspection apparatus that photo-electrically detects defects in the mouth of a bottle made of glass and the like.

2. Description of the Prior Art

Inspection at a bottle mouth portion of glass bottles or the like is an especially important item among those items of general inspection of glass bottles or the like. The reason is that such defects can cause a very dangerous situation should a human lip touch the bottle mouth and because serious problems are caused by fluid leakage occurring after filling the bottle with fluid and then capping the bottle mouth. Therefore, finest care is taken at the bottle mouth inspection even with new bottles, not to mention recycled bottles that are collected after initial use.

Various types of automatic inspection apparatuses for bottle mouth defects have been proposed in the art. In one of such inspection apparatus light is irradiated onto the bottle mouth portion, and when there is a defect such as a crack or chip at the bottle mouth portion, the irregularly reflected light from such defect portion is received by a photo-electric conversion sensor or the like to thereby sense such defect.

Further, in another one of the prior art inspection apparatus a substantially uniform light irradiation is applied to the top surface portion of the botle mouth, the reflected light from the top surface portion is picked up by a television camera or the like as a doughnut-shaped optical image corresponding to the ensire surface of the bottle mouth top, and then the doughnut-shaped optical image is compared to a standard optical image to thereby detect voids, dropouts or changes in the area, etc. of the doughnut-shaped optical image and hence defects of the bottle mouth.

According to the first of the above mentioned inspection methods there frequently occurs a situation wherein detection becomes difficult due to the fact that depending on the conditions of the cracks or chips at the bottle mouth, the irradiated lights thereon are difficult to be irregularly reflected. In the case of the latter flaw detection method wherein the doughnut-shaped optical image is used, there is a tendency to miss the detection of small flaws due to the fact that the bottles themselves are not precision industrial components and hence the bottle mouth shapes vary rather extensively. As a result it is difficult to set a constant standard for the doughnut-shaped optical image.

OBJECTS AND SUMMARY OF THE INVENTION

It is an object of the present invention to provide a bottle mouth defect inspection apparatus which is free from the faults of the aforementioned conventional inspection apparatuses.

It is another object of the present invention to provide a defect inspection apparatus especially effective for the mouth portion of a bottle made of glass.

It is a further object of the present invention to provide a bottle mouth defect inspection apparatus which photo-electrically detects the existence or not of a defect on the bottle mouth.

SUMMARY OF THE INVENTION

According to an aspect of the present invention, there is provided a bottle mouth defect inspection apparatus comprising:

(a) ring-shaped light source melans for irradiating a ring-shaped bottle mouth portion to be inspected;

(b) photo-electric conversion sensor means for converting a reflected light from said bottle mouth portion into an electrical signal; and (c) electronic processor means for processing said electrical signal to thereby inspect the existence or not of defects on said bottle mouth portion, wherein a diameter of said ring-shaped light source means is selected larger than an outer diameter of said bottle mouth portion; the optical axis of said photo-electric conversion sensor means, the center axis of said ring-shaped light source means and the center axis of the bottle mouth portion being coincident to each other; the position of each of said photo-electric conversion sensor means, said ring-shaped light source means and said bottle mouth portion along said coincident axis being selected such that a pair of ring-shaped reflected lights from an outer edge as well as the inner edge of said bottle mouth respectively are incident on said photo-electric conversion sensor means as a dual ring-shaped light for conversion to an electrical signal said electrical signal being processed by said electronic processor means to thereby detect the existence or not of the defects.

These and other objects, features and advantages of the present invention will become apparent from the following detailed description of the preferred embodiment taken in conjunction with the accompanying drawings, throughout which like references or numerals designate like elements and parts.

DESCRIPTION OF THE PREFERRED EMBODIMENT

The present invention will be explained hereunder in reference with the attached drawings.

Figure 1:
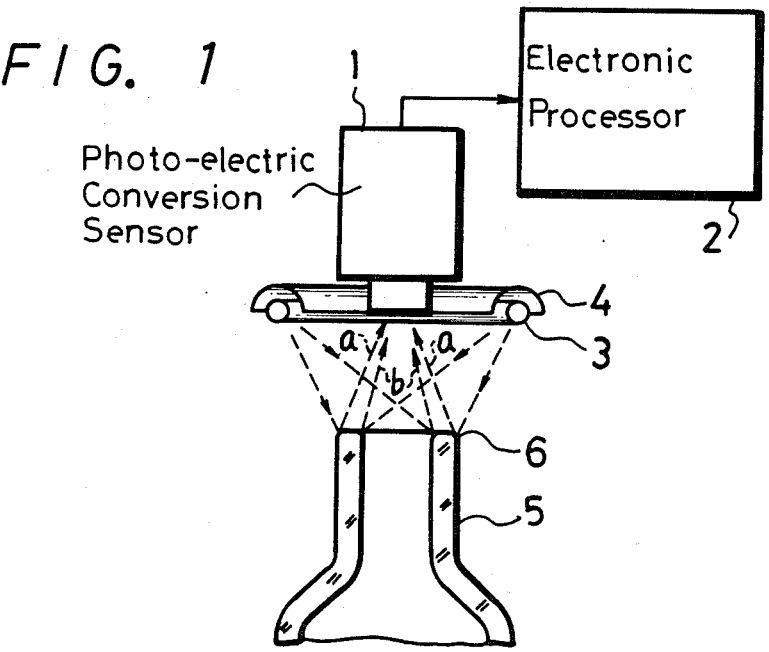
FIG. 1 is a schematic diagram showing an embodiment of the present invention.

FIG. 1 is a schematic diagram showing one embodiment of the present invention. In FIG. 1, reference numeral 1 designates a photo-electric conversion sensor such as a television camera which converts an optical image into an electrical signal, 2 an electronic processor which receives the electrical signal from the photo-electric conversion sensor 1 and carries out a predetermined electronic processing, and when a defect is detected, it delivers, for example, a defective product rejection signal or the like. Reference numeral 3 is a ring-shaped or circular light source that has a diameter larger than the outer diameter of a bottle mouth 6 of a bottle 5 to be inspected and which irradiates the bottle mouth 6 uniformly from the above. Reference numeral 4 is a ring-shaped light reflector that prevents light irradiation from scattering in unnecessary directions while it effectively uses the light emitted from the ring-shaped light source 3 in illuminating the bottle mouth. Further, the video camera 1 is located such that its optical axis coincides with the center axis of the light source 3 and that of the inspected bottle 5 and the video camera 1 can uniformly receive the reflected light from the bottle mouth 6.

The position of the video camera 1, ring-shaped light source 3 and bottle mouth 6 are selected such that as shown on FIG. 1, so that a ring-shaped or frustoconical reflected light a from the vicinity of the outer edge of bottle mouth 6 and a ring-shaped or frustoconical reflection light b from the vicinity of the inner edge of bottle mouth 6 both arrive at the video camera 1. On the other hand whereas the reflected light from the bottle mouth portion between the outer and inner edges of bottle mouth 6 does not reach the video camera 1. Thus, the video camera 1 photo-senses only the concentric double-circled and ring-shaped lights a and b.

In other words, the diameter of the ring-shaped light source is larger than that of the bottle mouth 6 and the video camera 1, the light source and the bottle mouth and video camera are arranged such that the light from the light source 3 which arrives at the frontal ring-shape portion of the bottle mouth 6, between its inner and outer edges, is reflected in a regular manner so that it does not in fact reach the camera 1. On the other hand, the light propagated from the inner and outer edges is irregularly reflected from these parts so that the ring-shaped reflections (a) and (b) are incident upon the video camera 1. Further, as will be shown in FIGS. 2b to 2e, the existance of flaws on the frontal ring-shaped portion of the bottle mouth 6, creates scattering of light so that the light is irregularly reflected from the flaws onto the video camera 1.

Figure 2A:
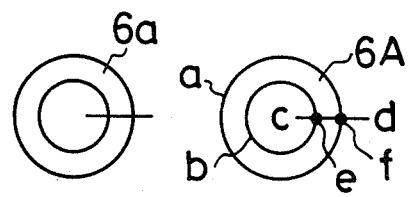
FIGS. 2A to 2F are schematic diagrams used to explain the operation of the embodiment shown in FIG. 1.
Figure 2A:
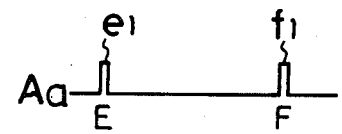
Figure 2B:
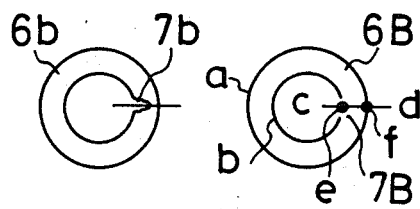
Figure 2B:
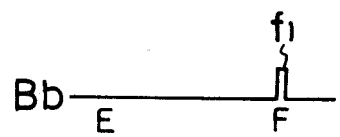
Figure 2C:
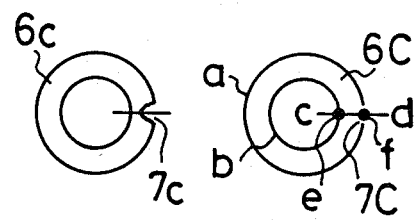
Figure 2C:
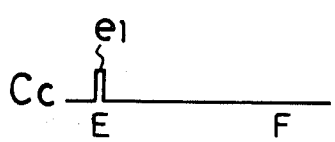
Figure 2D:
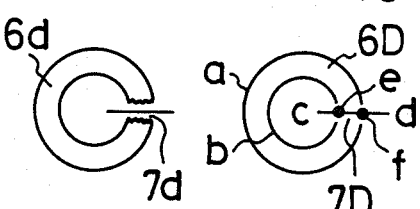
Figure 2D:
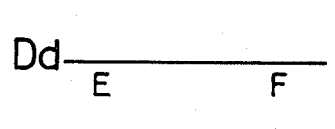
Figure 2E:
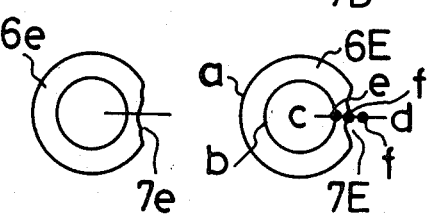
Figure 2E:
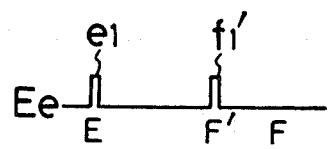
Figure 2F:
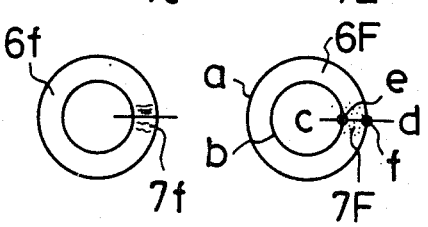
Figure 2F:
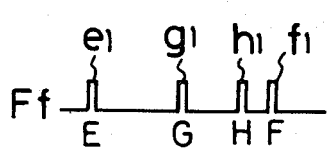

Such phenomenon will be now explained in reference with FIGS. 2A to 2F which illustrate in Column I several bottle mouths 6a–6f, in Column II the corresponding optical images received by the photoelectric sensor, and in Column III corresponding electrical signals. In FIG. 2A, 6a indicates a bottle mouth without any defect, while 6b to 6f in FIGS. 2B to 2F show bottle mouths that have defects 7b to 7f respectively. The bottle mouth 6a without defects, as shown on FIG. 2A forms a pair of annular rings at a certain distance corresponding to the width of the top surface of the bottle mouth 6. On the other hand, in FIG. 2B the bottle mouth 6b having a crack 7b at the inner edge of the bottle mouth; FIG. 2C shows a bottle mouth 6c with a crack 7c at the outer edge of the bottle mouth; FIG. 2D shows a bottle mouth 6d that has a crack 7d which crosses the bottle mouth from its outer edge portion to its inner edge portion; FIG. 2E shows a bottle mouth 6e that has a crack 7e that is smooth but largely void at the outer edge portion of the bottle mouth; and FIG. 2F shows a bottle mouth 6f that has no void but has the fine scuffy mark 7f on the top surface of the. Of course, there are many other variations in the types of defects at bottle mouth 6 and FIG. 2 illustrates typical examples only, in order to explain the defect detection.

FIGS. 2A to 2F also show the optical images 6A–6F corresponding to the respective bottle mouth 6a to 6f as they are incident on the video camera 1. These optical images 6A to 6F are respectively the dual ring-shaped optical images as formed by the ring-shaped reflection lights a and b that are reflected from the areas of the inner and outer edges of bottle mouth portions 6a to 6f.

Numerals 7B to 7F illustrate the manner by which the optical images 6B to 6F are sensed to obtain the indication of the respectively to defects 7b to 7f on bottle mouths 6b to 6f. In this case, a straight line $\overline{cd}$ that passes through the center of the dual ring-shaped reflection lights b and a of the optical images 6A to 6F, respectively, is considered and the crossing points of this straight line $\overline{cd}$ with the reflected lights b and a are respectively taken as points e and f. If the bottle mouth 6 has no defects, these points e and f would constitute shining points because reflection of lights b and a would both arrive thereat. Further, the reflection of the light will not reach any other points than points e and f on the straight line $\overline{cd}$. On FIGS. 2A to 2F, waveform diagrams Aa to Ff at the right sides of optical images 6A to 6F respectively show the light disributions along the above straight line $\overline{cd}$ corresponding to the above optical images 6A to 6F. Since optical image 6A does not have any defect, as shown by the waveform diagram Aa, pulses e1 and f1 corresponding to light points e and f appear at points E and F of the signal waveform. Each straight line $\overline{cd}$ related to each of the optical images 6B to 6F passes through each of the optical defects 7B to 7F of the optical images 6B to 6F as shown on the drawing, so that the light distributions along the straight lines $\overline{cd}$ of the optical images 6B to 6F appear as shown on the responsive waveforms Bb to Ff at the right side thereof. In other words, as to the optical image 6B, at the spot portion of the point e on the straight line $\overline{cd}$ there is no light due to the existence of the optical defect 7B so that as shown on the waveform Bb, light f1 only appears at point F; in the same respect, as for the optical image 6C, due the optical defect 7C, as shown on the waveform Cc, light e1 only appears at point E; for the case of optical image 6D, due to the optical defect 7D, as shown on the waveform Dd, no light appears at both points E and F; in the case of optical image 6E, due to the optical defect 7E, as shown on waveform Ee, lights e1 and f1' appear at responsive points E and F' corresponding to point 3 and its nearby point f' on the straight line $\overline{cd}$ (of course, no light appears at point F); and in the case of optical image 6F, due to the optical defect 7F which responds to scuffy 7f, as shown on the waveform Ff, other than the lights e1 and f1 at points E and F, lights g1 and h1 appear at points such as G and H which are located between points E and F as noises. In these cases, the intensity of each of the lights that appear at respective points E, F, F' G and H can be assumed substantially equal.

Now then, since the video camera 1 converts light into an electrical signal, when optical images such as 6A to 6F as shown on FIGS. 2A to 2F are photo-sensed or picked up, in relation to the straight line $\overline{cd}$, it delivers pulse-shaped electrical signals that correspond to the waveforms Aa to Ff. In this case, the generation positions of the electrical signals as well as the levels thereof are the exact same as those of the lights e1, f1, f1', g1 and h1 as shown on waveforms Aa to Ff, so that hereunder the corresponding electrical signals from the video camera 1 will be represented by these pulses.

Further, the waveforms Aa to Ff on FIGS. 2A to 2F show the responsive electrical signals of the respective optical images 6A to 6F along the straight lines $\overline{cd}$, but in fact, if bottle 5 and accordingly bottle mouth 6 is rotated on turn so that the straight line $\overline{cd}$ passes through the entire circumference of the bottle mouth 6 or if the inspection points, namely the straight line $\overline{cd}$ is moved electronically so that it passes the entire circumference of the optical images 6A to 6F of bottle mouth portion 6, the electrical signals corresponding to the entire circumference of each of the optical images can be obtained from the video camera 1.

Figure 3:
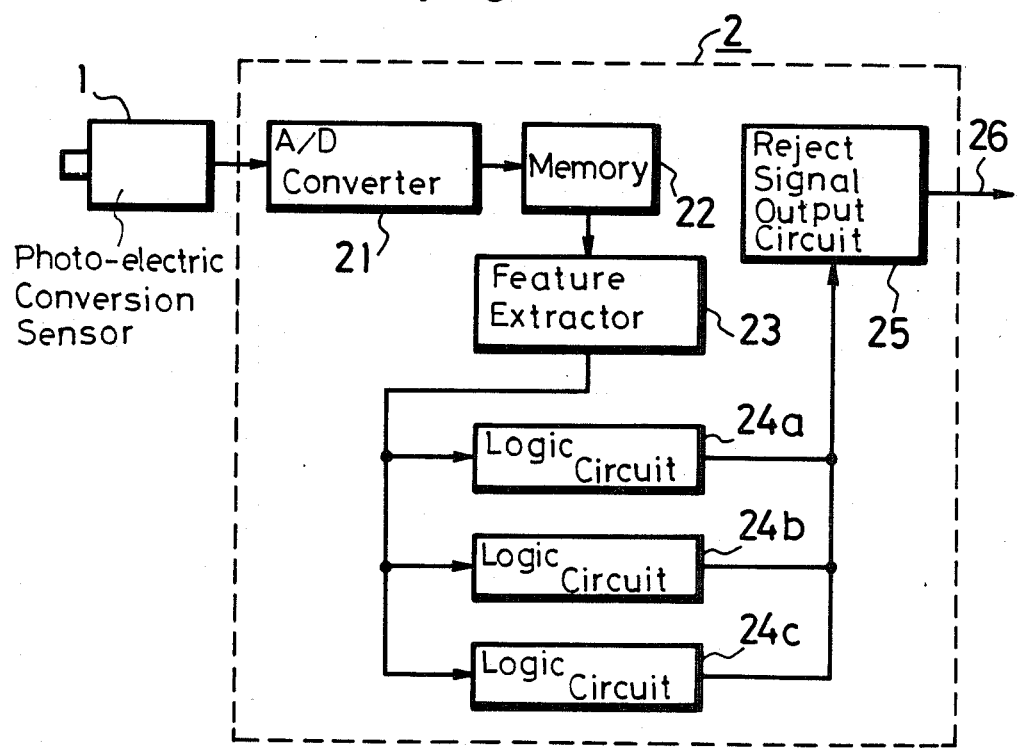
FIG. 3 is a block diagram showing one example of the electronic processor as indicated on FIG. 1.

Turning to FIG. 3, one example of the above mentioned electronic processor 2 will be explained. This electronic processor 2 is, for example, a computor that processes the electrical signal from photo-electric conversion sensors 1 such as a video camera and then judges the existence or not of defects in the object picked up by the video camera 1. Needless to say, without relying upon the computor, the electronic processor 2 may freely be assembled by arranging the proper logics in its hardware only.

As shown on FIG. 3, in this example, the output electrical signal from the video camera 1 is converted into a digital signal by an A/D (analog-to-digital) converter 21. This digital signal is supplied to a memory 22, in which it is temporarily memorized. This memory 22 normally accumulates the data for one frame, so that it is called a frame memory or the like. Next, the data accumulated in memory 22 are passed through a feature extractor 23 in sequence and then simultaneously distributed or supplied to logic circuits 24a, 24b and 24c. Here, the feature extractor 23 is such a circuit which is functions to distinctly brings out the data that respond to the dual ring-shaped lights of optical images 6A to 6F, and as a conventional example, may be a comparator or the like. If the data from the memory 22 is passed through this comparator 23, only the portion of the data or electrical signal corresponding to the dual ring-shaped light higher than a predetermined level is derived from the comparator 23. Then, only the data of the optical image of the dual ring-shaped light is delivered from the comparator 23 but the unnecessary data are not delivered from the comparator 23.

The signal passed through the feature extractor or comparator 23 is supplied to the logic circuits 24a, 24b and 24c in which the mutual relaiton of the dual ring-shaped lights as mentioned with FIG. 2 is checked. For instance, the logic circuit 24a is used to check whether the two signals e1 and f1 that correspond to the dual ring-shaped lights of optical images 6A to 6D are completely present or not; logic circuit 24b checks, as in the case of optical image 6E, whether the distance between signals e1 and f1' is the same to a predetermined distance or not; and further, logic circuit 24c checks, as in the case of optical image F, whether or not noise signals g1 and h1 are produced between the signals e1 and f1, respectively. If any abnormality is acknowledged by any of the logic circuits 24a to 24c, such logic circuit delivers an output signal. The output terminals of all the logic circuits 24a, 24b and 24c are commonly connected to the input terminal of reject signal output circuit 25. This output circuit 25 is so constructed that even if either one of the logic circuits 24a to 24c delivers the output signal, the reject signal output circuit 25 delivers a control signal 26. This control signal 26 is used to drive a defective product detection alarm system or defective product reject mechanism though not shown in FIG. 3.

The above mentioned logic is available by a simple programing of the computer softwar. While, when the same logic is to be conducted by hardware, it is apparent that the hardware can be easily constructed by the use of a clock signal and a counter.

As set forth above, according to the present invention, when the defects on the bottle mouth portion is inspected, the defects over a wide area or on the vicinities of the outer and inner edges of the bottle mouth and on the upper surface of the bottle mouth between its outer and inner edges can be positively detected. In addition, according to the invention, complicated logic to calculate, for example, the area of the bottle mouth portion and so on are not required but such circuit can be performed by only a simple logic circuit, so that the inspection apparatus is simple in construction and hence can be made at low cost. Further, in this invention a conventional irradiation lamp is employed, so that this invention can be practised easily.

It will be apparent that without escaping the scope of the novel concepts of the present invention, any concern skilled in the art may conduct many variations and changes so that the scope of the invention should be determined by the appended claims only.

I claim as my invention:

1. Apparatus for inspecting the mouth of bottles for defects, comprising:

a ring-shaped light source having a diameter larger than the outer diameter of the mouth of the bottle for illuminating the mouth of the bottle and for being reflected therefrom;

a photoelectric conversion sensor for sensing the light reflected from the mouth of said bottle said light source, said bottle and said sensor being arranged so that the reflection of only of the inner and outer edges of the mouth of said bottle is incident on said sensor as a pair of concentric ring-shaped images, said sensor converting said images into corresponding electrical signals;

an electronic processor comprising means for extracting from said electronic signals and features of each of said concentric layers crossing a radial line passing through the common center and means for determining the mutual relationship of said features and producing an output thereof from which defects in the mouth of said bottle are detected.

2. The apparatus according to claim 1 wherein said photoelectric conversion sensor, the right-shaped light source, and the bottle are located so that the optical axis of the photoelectric conversion sensor, the central axis of the ring-shaped light source, and the central axis of the bottle mouth are coincident with each other.

3. The apparatus according to claim 2 wherein said electronic processor includes and A/D converter for converting the electrical signal from said photoelectric conversion sensor to a digital signal, memory means for temporarily storing said digital signal from said A/C converter, and feature extractor means for producing, on the basis of the data from said memory means, data corresponding to the pair or ring-shaped images at two intersecting points on the radial line passing through the common center and having a plurality of logic circuit means for receiving the data from said feature extractor, checking the mutual relationship of the data for each image, and producing said output signal if said mutual relationship is abnormal.

4. The apparatus according to claim 3 further comprising reject signal output circuit means whose input terminal is connected to output terminals of the plurality of logic circuit means, whereby when any one of said plurality of logic circuit means produces the output signal, said reject signal output circuit means produces a signal.

5. The apparatus according to claim 3 wherein said electronic processor includes means for sequentially extracting data along a series of radial lines rotatively about the common center.

6. The apparatus according to claim 5 including means for causing said radial line to rotatively sweep circumferentially about said pair of images.

* * * * *

UNITED STATES PATENT AND TRADEMARK OFFICE
CERTIFICATE OF CORRECTION

PATENT NO. : 4,775,889

DATED : October 4, 1988

INVENTOR(S) : HAJIME YOSHIDA

It is certified that error appears in the above-identified patent and that said Letters Patent is hereby corrected as shown below:

Column 6, line 32 replace "layers" with --images-- line 36 replace "right" with --ring-- line 47 replace "A/C" with --A/D--

Signed and Sealed this

Fourth Day of April, 1989

Attest:

DONALD J. QUIGG

Attesting Officer

Commissioner of Patents and Trademarks